United States Patent
Cho et al.

(10) Patent No.: US 9,320,718 B2
(45) Date of Patent: Apr. 26, 2016

(54) MULTILAYER COATING FORM OF ORALLY ADMINISTERED PHARMACEUTICAL COMPOSITION CONTAINING OMEGA-3 FATTY ACID OR ALKYL ESTER THEREOF AND STATIN BASED DRUG

(71) Applicant: KUHNIL PHARM. CO., LTD., Chungcheongnam-do (KR)

(72) Inventors: Jae-Pyoung Cho, Gunpo-si (KR); Pung-Sok Lee, Yongin-si (KR); Seul-A Lee, Gwangmyeong-si (KR); Min-Ho Jeong, Uijeongbu-si (KR); Mase Lee, Goyang-si (KR)

(73) Assignee: KUHNIL PHARM. CO., LTD., Cheonan-si (KR)

( * ) Notice: Subject to any disclaimer, the term of this patent is extended or adjusted under 35 U.S.C. 154(b) by 0 days.

(21) Appl. No.: 14/403,548

(22) PCT Filed: May 21, 2013

(86) PCT No.: PCT/KR2013/004430
§ 371 (c)(1),
(2) Date: Nov. 24, 2014

(87) PCT Pub. No.: WO2013/176455
PCT Pub. Date: Nov. 28, 2013

(65) Prior Publication Data
US 2015/0086624 A1     Mar. 26, 2015

(30) Foreign Application Priority Data

May 22, 2012 (KR) .......................... 10-2012-0054351

(51) Int. Cl.
| | |
|---|---|
| *A61K 9/48* | (2006.01) |
| *A61K 31/47* | (2006.01) |
| *A61K 31/505* | (2006.01) |
| *A61K 31/23* | (2006.01) |
| *A61K 31/40* | (2006.01) |

(52) U.S. Cl.
CPC ............ *A61K 9/4891* (2013.01); *A61K 9/4816* (2013.01); *A61K 31/23* (2013.01); *A61K 31/40* (2013.01); *A61K 31/47* (2013.01); *A61K 31/505* (2013.01); *A61K 9/4808* (2013.01)

(58) Field of Classification Search
None
See application file for complete search history.

(56) References Cited

U.S. PATENT DOCUMENTS

| | | | |
|---|---|---|---|
| 2003/0180352 A1* | 9/2003 | Patel et al. .................... | 424/465 |
| 2007/0212411 A1 | 9/2007 | Fawzy et al. | |
| 2010/0029743 A1* | 2/2010 | Agrawal et al. .............. | 514/423 |

FOREIGN PATENT DOCUMENTS

| | | |
|---|---|---|
| KR | 10-2007-0083715 A | 8/2007 |
| KR | 10-2007-0038553 A | 10/2007 |
| KR | 10-2007-0108945 A | 11/2007 |
| KR | 10-2009-0086078 A | 8/2009 |
| WO | 2008/000731 A2 | 1/2008 |
| WO | 2009087938 A1 | 7/2009 |
| WO | 2010/069951 A1 | 6/2010 |

OTHER PUBLICATIONS

PCT International Search Report and Written Opinion in International Application No. PCT/KR2013/004430, mailed Sep. 26, 2013.
Bays, H.E. et al., "Effects Of Prescription Omega-3-Acid Ethyl Esters On Non-High-Density Lipoprotein Cholesterol When Coadministrated With Escalating Doses Of Atorvastatin", Mayo. Clin. Proc., vol. 85, Issue 2, Feb. 2010, pp. 122-128.
Bays, H.E. et al., "Prescription omega-3 fatty acids and their lipid effects: physiologic mechanisms of action and clinical implications", Expert Rev. Cardiovasc. Ther., vol. 6, Issue 3, Mar. 2008, pp. 391-409.
Chan, D.C. et al., "Factorial study of the effects of atorvastatin and fish oil on dyslipidaemia in visceral obesity", Eur. J. Clin. Invest., vol. 32, Issue 6, Jun. 2002, pp. 429-436.
Farooqui, A. et al., "Comparison of biochemical effects of statins and fish oil in brain: The battle of titans", Brain Research Reviews, 2007, vol. 56, pp. 443-471.
Maki, K.C. et al., "Omega-3 Fatty Acids for the Treatment of Elevated Triglycerides", Olin Lipidology, vol. 4, Issue 4, 2009, pp. 425-437.
Yigeumsu, et al. "Comparison of Rosuvastatin plus Omega-3 fatty acids combination therapy and Rosuvastatin monotherapy in the treatment of type II hypercholesterolemia", Institute of Medicine, Release 75, No. 2s, Journal of Medicine, 2008, S-211, p. S 456.
Extended European Search Report in European Application No. 13794039.1, dated Dec. 16, 2015.

* cited by examiner

*Primary Examiner* — Robert A Wax
*Assistant Examiner* — Randeep Singh
(74) *Attorney, Agent, or Firm* — Nixon Peabody LLP

(57) ABSTRACT

A pharmaceutical composition in multilayer-coated form including an omega-3 fatty acid or an alkyl ester thereof and a statin-based drug, and more particularly, a pharmaceutical composition for oral administration including: (a) a gelatin capsule core containing an omega-3 fatty acid or an alkyl ester thereof; (b) a first coating layer formed by coating, on the gelatin capsule core, hydroxypropyl methylcellulose and a copolymer of butyl methacrylate, (2-demethylaminoethyl) methacrylate, and methyl methacrylate at a weight ratio of 1:2:1; and (c) a second coating layer formed by coating, on the first coating layer, a coating solution containing a statin-based drug.

14 Claims, No Drawings

MULTILAYER COATING FORM OF ORALLY ADMINISTERED PHARMACEUTICAL COMPOSITION CONTAINING OMEGA-3 FATTY ACID OR ALKYL ESTER THEREOF AND STATIN BASED DRUG

CROSS-REFERENCE TO RELATED PATENT APPLICATIONS

This application is a National Phase of International Application No. PCT/KR2013/004430, filed on May 21, 2013, entitled MULTILAYER COATING FORM OF ORALLY ADMINISTERED PHARMACEUTICAL COMPOSITION CONTAINING OMEGA-3 FATTY ACID OR ALKYL ESTER THEREOF AND STATIN BASED DRUG, which claims the benefit of Korean Patent Application No. 10-2-12-0054351, filed May 22, 2012, the contents of which are incorporated herein by reference in their entirety.

TECHNICAL FIELD

The present disclosure relates to a pharmaceutical composition in multilayer-coated form that includes an omega-3 fatty acid or an alkyl ester thereof and a statin-based drug, and more particularly, to a pharmaceutical composition in multilayer-coated form that includes a shield coating layer of a specific polymer disposed between a gelatin capsule core including an omega-3 fatty acid or an alkyl ester thereof and a drug-coating layer including a statin-based drug.

BACKGROUND ART

An omega-3 fatty acid is also referred to as an omega-3 unsaturated fatty acid, an omega-3 highly unsaturated fatty acid, or a polyunsaturated fatty acid (PUFA). Typical examples thereof are docosahexaenoic acid (DHA), eicosapentaenoic acid (EPA), arachidonic acid (ARA), docosapentaenoic acid, α-linolenic acid, and combinations thereof. An omega-3 fatty acid may be used in an alkyl ester form thereof, for example, DHA or EPA, for example, as an ethyl ester of DHA or EPA. Pharmaceutical products including about 90% or more of omega-3 fatty acid ethyl ester (usually referred to as "omega-3-acid ethyl esters 90") as an active ingredient are current commercially available under the product name "Omacor™" or "LOVAZA™" in the market, including Korea, Europe, and U.S.A. An omega-3 fatty acid or an alkyl ester thereof is used for the treatment of patients with a mixed type of hypercholesterolemia and hypertriglyceridemia (type IIb) at uncontrollable triglyceride levels.

A statin-based drug is a 3-hydroxy-3-methylglutaryl-coenzyme (HMG-CoA) reductase inhibitor, and used to lower blood cholesterol levels. Examples of statin-based drugs include simvastatin, atorvastatin, rosuvastatin, lovastatin, pitavastatin, cerivastatin, fluvastatin, mevastatin, and pravastatin.

There has been active research into co-administration of an omega-3 fatty acid such as omega-3-acid ethyl ester 90, and a statin-based drug. For example, the co-administration of omega-3-acid ethyl ester 90 and atorvastatin (for example, Lipitor™) is reported to be more efficient to control blood total cholesterol, triglyceride (TG), and very low-density lipoprotein (VLDL) levels, compared to the administration of atorvastatin alone (Bays, H. E. B., et al., Effects of prescription omega-3-acid esters on non-high-density lipoprotein cholesterol when administered with escalated doses of atorvastatin. *Mayo. Clin. Proc.*, 85, 122-128 (2010)). Co-administration of omega-3-acid ethyl ester 90 and atorvastatin is reported to have a synergistic effect on improving TG, high-density lipoprotein (HDL), and cholesterol levels, compared to the administration of omega-3-acid ethyl ester 90 or atorvastatin alone (Chan, D. C., et al., Factorial study of the effects of atorvastatin and fish oil on dyslipidaemia in visceral obesity. *Eur. J. Clin., Invest.*, 32, 429-436, 2002). Reportedly, the co-administration of omega-3-acid ethyl ester 90 and rosuvastatin results in an improved liquid profile compared to the monotherapy, and also could be used as an alternative therapy for patients with mixed hyperlipidemia (Lee, S. U., et al., Comparison of rosuvastatin plus omega-3 fatty acids combination therapy and rosuvastatin monotherapy in the treatment of mixed hyperlipidemia: An 8-week randomized trial. Atherosclerosis supplement, 2009, Vol. 10, p. 489). Reportedly, the co-administration of Omacor™ and a statin-based drug may improve a lipid profile in patients with persistent hypertriglyceridemia, compared to the monotherapy, which is attributed to the LDL and VLDL improvement effects of a statin-based drug and reduced secretion of VLDL in the liver due to omega-3-acid ethyl ester 90 (Bays, H., et al., Prescription omega-3 fatty acids and their lipid effects: physiological mechanisms of action and clinical implications, *Expert Review of Cardiovascular Therapy*, 2008, 6(3), 391-409; and Maki, K. C., et al., Omega-3 fatty acids for the treatment of elevated triglycerides *Clin Lipidology*, 2009, 4(4). 425-437). In addition, it was reported that the co-administration of EPA as an ingredient of omega-3-acid ethyl ester 90 with a statin-based drug may significantly improve total serum cholesterol and TG levels and increase HDL levels in patients with cardiovascular disease, and thus may be an efficient therapy to treat hyperlipidemia (Farooqui, A., et al., Comparison of biochemical effects of statin and fish oil in the brain: The battle of titans. *Brain Research Reviews*, 2007, 56, 443-471).

There have been attempts to develop composite formulations including an omega-3 fatty acid, such as omega-3-acid ethyl ester 90, and a statin-based drug. For example, Korea Patent Publication No. 10-2007-0038553 discloses a pharmaceutical composition including an omega-3 fatty acid and a statin-based drug (pravastatin). According to the disclosure, the stability of this formulation is highly dependent on types of salts, and about 3% of lactone and about 2% to about 3% of other degradation products may be generated. Korea Patent Publication No. 10-2007-0083715 discloses a suspension including a microcapsule consisting of a statin-based drug (for example, simvastatin) and a polymer in order to ensure the stability of the statin-based drug. Korea Patent Publication No. 10-2007-0108945 discloses a pharmaceutical composition in a homogeneous solution form that includes a statin-based drug in a solvent system including omega-3 fatty acid, but with about less than 10% of the statin-based drug remaining undissolved in the solvent system, due to the failure of complete dissolution of the statin-based drug in the solvent system.

DISCLOSURE

Technical Problem

The present disclosure provides a pharmaceutical composition in multilayer-coated form that fundamentally blocks contact between an omega-3 fatty acid and a statin-based drug. The present inventors found that upon forming a drug-coating layer including the statin-based drug on a gelatin capsule core including the omega-3 fatty acid by aqueous coating (for example, using a 20% aqueous ethanol solution), the coating process is not substantially possible due to adhering of gelatin capsule cores to each other and the shape deformation of the gelatin capsule cores may occur during the coating process. However, the present inventors also found that these problems in the coating process may be resolved by introducing a shield coating layer including a specific polymer. The present inventors also investigated various kinds of coating agents having good compatibility with the statin-based drug, and found that designing a drug-coating layer including a statin-based drug with a specific coating agent therefor may improve the stability.

Therefore, the present disclosure provides a pharmaceutical composition for oral administration that includes a gelatin capsule core including an omega-3 fatty acid or an alkyl ester thereof; a specific shield coating layer; and a drug coating layer including a statin-based drug.

Technical Solution

According to an aspect of the present disclosure, there is provided a pharmaceutical composition for oral administration, including: (a) a gelatin capsule core containing an omega-3 fatty acid or an alkyl ester thereof; (b) a first coating layer formed by coating, on the gelatin capsule core, hydroxypropyl methyl cellulose and a copolymer of butyl methacrylate, (2-demethylaminoethyl) methacrylate, and methyl methacrylate at a weight ratio of 1:2:1; and (c) a second coating layer formed by coating, on the first coating layer, a coating solution containing a statin-based drug.

The alkyl ester of an omega-3 fatty acid may be an ethyl ester of an omega-3 fatty acid.

A weight ratio of the hydroxypropyl methyl cellulose and the copolymer of butyl methacrylate, (2-demethylaminoethyl) methacrylate, and methyl methacrylate at a weight ratio of 1:2:1 in the first coating layer may be in a range of about 1:0.8 to about 1:10, and in some embodiments, in a range of about 1:1 to about 1:9.

The coating solution containing a statin-based drug may be obtained by dissolving atorvastatin or a salt thereof, and at least one coating agent selected from the group consisting of polyethylene glycol, sodium alginate, hydroxypropyl methyl cellulose, and polyvinyl alcohol in water, ethanol, or an aqueous ethanol solution. The amount of the coating agent may be in a range of about 1 part by weight to about 20 parts by weight based on 1 part by weight of the atorvastatin or a salt thereof.

The coating solution containing a statin-based drug may be obtained by dissolving rosuvastatin or a salt thereof, and at least one coating agent selected from the group consisting of hydroxypropyl methyl cellulose, ethyl cellulose, and polyvinyl alcohol in water, ethanol, or an aqueous ethanol solution. The amount of the coating agent may be in a range of about 1 part to about 20 parts by weight based on 1 part by weight of the rosuvastatin or a salt thereof.

The coating solution containing a statin-based drug may be obtained by dissolving pitavastatin or a salt thereof and hydroxypropyl methyl cellulose in water, ethanol, or an aqueous ethanol solution. The amount of the hydroxypropyl methyl cellulose may be in a range of about 1 part to about 50 parts by weight based on 1 part by weight of the pitavastatin or a salt thereof.

The second coating layer may further include at least one antioxidant selected from the group consisting of tocopherol, di-alpha-tocopheryl polyethylene glycol 1000 succinate, and tocopheryl acetate. The amount of the antioxidant may be in a range of about 0.1 part to about 1 part by weight based on 1 part by weight of the statin-based drug.

The pharmaceutical composition for oral administration according to any of the above-described embodiments may further include a third coating layer formed by coating, on the second coating layer, a coating solution containing at least one coating agent selected from the group consisting of hydroxypropyl cellulose, hydroxypropyl methyl cellulose, a copolymer of butyl methacrylate, (2-demethylaminoethyl) methacrylate, and methyl methacrylate at a weight ratio of 1:2:1, carboxymethyl cellulose, polyvinyl alcohol-polyethylene glycol copolymer, polyvinyl acetate, and polyvinyl alcohol. The coating solution for the third coating layer may further include at least one light-shielding agent selected from the group consisting of talc, carnauba wax, ethyl vanillin, titanium oxide, and iron oxide.

Advantageous Effects

As described above, according to the one or more embodiments of the present disclosure, a pharmaceutical composition in multilayer-coated form introduces a shield coating layer including a specific polymer disposed between a gelatin capsule layer including an omega-3 fatty acid or an alkyl ester thereof and a drug-coating layer including a statin-based drug, thereby fundamentally blocking deformation of a gelatin capsule core and adhesion of gelatin capsule cores to each other that may occur during the formation of the drug-coating layer including a satin-based drug by aqueous coating. The pharmaceutical composition in multilayer-coated form according to any of the embodiments may include a statin-based drug-containing drug-coating layer including a coating agent that is highly compatible with the statin-based drug, and thus may have improved stability.

MODE FOR INVENTION

As used herein, the term "an omega-3 fatty acid" may refer to any of an omega-3 (ω-3) unsaturated fatty acid, an omega-3 highly unsaturated fatty acid, and a polyunsaturated fatty acid (PUFA). Examples of an omega-3 fatty acid include docosahexaenoic acid (DHA), eicosapentaenoic acid (EPA), arachidonic acid (ARA), docosapentaenoic acid, α-linolenic acid, and combinations thereof. The term "an alkyl ester of omega-3 fatty acid" may refer to a derivative of an omega-3 fatty acid with an alkyl group linked thereto by an ester bond, for example, an ethyl ester of DHA, an ethyl ester of EPA, or combinations thereof. Other examples of an alkyl ester of omega-3 fatty acid include 90% or more of an ethyl ester of omega-3 fatty acid, commonly referred to as "omega-3-acid ethyl esters 90", which is an active ingredient of Omacor™ or LOVAZA™ In one or more embodiments of the present disclosure, a pharmaceutical composition of oral administration may include a therapeutically effective amount of omega-3 fatty acid or omega-3-acid ethyl ester 90. The therapeutically effective amount herein may be about 1,000 mg a unit dosage form, but is not limited thereto.

As used herein, the term "statin-based drug" may include simvastatin or a salt thereof (for example, an ammonium salt, a sodium salt, or the like), atorvastatin or a salt thereof (for example, a calcium salt, a sodium salt, or the like), rosuvastatin or a salt thereof (for example, a calcium salt, a sodium salt, a methylamine salt, a zinc salt, a strontium salt, a barium salt, a cadmium salt, a cesium salt, or the like), lovastatin or a salt thereof (for example, a sodium salt, an ammonium salt, or the like), pitavastatin or a salt thereof (for example, a calcium salt, a sodium salt, or the like), cerivastatin or a salt thereof (for example, a sodium salt, or the like), fluvastatin or a salt thereof (for example, a sodium salt, or the like), mevastatin or a salt thereof (for example, a sodium salt, or the like), pravastatin or a salt thereof (for example, a sodium salt, a tert-octylamine salt, or the like), but is not limited thereto. For example, the statin-based drug may be selected from the group consisting of rosuvastatin or a salt thereof, atorvastatin or a salt thereof, and pitavastatin or a salt thereof. In one or more embodiments of the present disclosure, the pharmaceutical composition may include a therapeutic effective amount of the statin-based drug, which may be easily determined based on disclosed references. For example, the pharmaceutical composition may include about 5 mg rosuvastatin or a salt thereof, about 5 mg of atorvastatin or a salt thereof, or about 2 mg of pitavastatin or a salt thereof in a unit dosage form. However, embodiments are not limited thereto.

According to an aspect of the present disclosure, a pharmaceutical composition for oral administration, including: (a) a gelatin capsule core containing an omega-3 fatty acid or an alkyl ester thereof; (b) a first coating layer formed by coating, on the gelatin capsule core, hydroxypropyl methyl cellulose and a copolymer of butyl methacrylate, (2-demethylaminoeethyl) methacrylate, and methyl methacrylate at a weight ratio of 1:2:1; and (c) a second coating layer formed by coating, on the first coating layer, a coating solution containing a statin-based drug.

To design a pharmaceutical composition in multilayer-coated form that fundamentally blocks contact between an omega-3 fatty acid and a statin-based drug, the present inventors tested the applicability of aqueous coating processes. However, they found that upon forming a drug-coating layer including the statin-based drug on a gelatin capsule core including the omega-3 fatty acid by aqueous coating (for example, using a 20% aqueous ethanol solution), the coating process is not substantially possible due to adhering of gelatin capsule cores to each other and the shape deformation of the gelatin capsule cores may occur during the coating process. The present inventors also found that these problems in the coating process may be resolved by introducing a shield coating layer including a specific polymer. The polymer for the first coating layer may include hydroxypropyl methyl cellulose; and a copolymer of butyl methacrylate, (2-demethylaminoeethyl) methacrylate, and methyl methacrylate at a weight ratio of 1:2:1 (for example, Eudragit™ E, Eudragit™ E PO, or the like). A weight ratio of the hydroxypropyl methyl cellulose and the copolymer of butyl methacrylate, (2-demethylaminoeethyl) methacrylate, and methyl methacrylate at a weight ratio of 1:2:1 in the first coating layer may be in a range of about 1:0.8 to about 1:10, and in some embodiments, about 1:1 to about 1:9, and in some other embodiments, about 1:4.

The present inventors also investigated various kinds of coating agents having good compatibility with the statin-based drug, and found that designing a drug-coating layer including a statin-based drug with a specific coating agent therefor may improve the stability.

In some embodiments, the coating solution including a statin-based drug may be obtained by dissolving atorvastatin or a salt thereof, and at least one coating agent selected from the group consisting of polyethylene glycol, sodium alginate, hydroxypropyl methyl cellulose, and polyvinyl alcohol in water, ethanol, or an aqueous ethanol solution. The amount of the coating agent may be in a range of about 1 part by weight to about 20 parts by weight based on 1 part by weight of the atorvastatin or a salt thereof.

In some embodiments, the coating solution including a statin-based drug may be obtained by dissolving rosuvastatin or a salt thereof, and at least one coating agent selected from the group consisting of hydroxypropyl methyl cellulose, ethyl cellulose, and polyvinyl alcohol in water, ethanol, or an aqueous ethanol solution. The amount of the coating agent may be in a range of about 1 part to about 20 parts by weight based on 1 part by weight of the rosuvastatin or a salt thereof.

In some other embodiments, the coating solution including a statin-based drug may be obtained by dissolving pitavastatin or a salt thereof and hydroxypropyl methyl cellulose in water, ethanol, or an aqueous ethanol solution. The amount of the hydroxypropyl methyl cellulose may be in a range of about 1 part to about 50 parts by weight based on 1 part by weight of the pitavastatin or a salt thereof.

In some embodiments, the second coating layer of the orally administered pharmaceutical composition may further include at least one antioxidant selected from the group consisting of tocopherol, di-alpha-tocopheryl polyethylene glycol 1000 succinate, and tocopheryl acetate. The amount of the antioxidant may be in a range of about 0.1 part to about 1 part by weight based on 1 part by weight of the statin-based drug. In some other embodiments, the second coating layer may further include, for example, a stabilizer, an adsorbant, a pH adjuster, a plasticizer, or the like that are commonly used in the field of pharmaceutics. The stabilizer may include, for example, sodium bicarbonate, magnesium oxide, calcium silicate, sodium citrate, sodium phosphate, or the like, but is not limited thereto. The adsorbant may include, for example, sodium oleate, but is not limited thereto. The pH adjuster may include, for example, sodium hydroxide, but is not limited thereto. The plasticizer may include, for example, triethyl citrate, but is not limited thereto.

In some embodiments, the pharmaceutical composition for oral administration may further include a third coating layer that may minimize contact with oxygen and moisture to improve the stability of the statin-based drug. For example, the pharmaceutical composition for oral administration may further include a third coating layer formed by coating, on the second coating layer, a coating solution including at least one coating agent selected from the group consisting of hydroxypropyl cellulose, hydroxypropyl methyl cellulose, a copolymer of butyl methacrylate, (2-demethylaminoeethyl) methacrylate, and methyl methacrylate at a weight ratio of 1:2:1, carboxymethyl cellulose, polyvinyl alcohol-polyethylene glycol copolymer, polyvinyl acetate, and polyvinyl alcohol. The amount of the coating agent for the third coating layer may be within about 10 wt % of a total weight of the final capsule, for example, in a range of about 3 wt % to about 5 wt % of the total weight of the final capsule, but is not limited thereto. In some embodiments, the coating solution for the third coating layer may further include: at least one light-shielding agent selected from the group consisting of talc, carnauba wax, ethyl vanillin, titanium oxide, and iron oxide; and/or a pigment, for example, Red 40. The third coating layer may be formed by a common coating method using a coating solution prepared by dissolving a coating agent, a light-shielding agent, and/or a pigment in an appropriate solvent, for example, isopropyl alcohol, methanol, ethanol, acetone, distilled water, or a mixture thereof.

One or more embodiments of the present disclosure will now be described in detail with reference to the following examples. However, these examples are only for illustrative purposes and are not intended to limit the scope of the one or more embodiments of the present disclosure.

EXAMPLE 1

Evaluation of Compatibility of Rosuvastatin and Coating Material

To form a rosuvastatin-containing drug-coating layer, compatibility of rosuvastatin with various coating materials (coating agents and surfactants) were evaluated. About 2.5 mg of each coating material as shown in Table 1 was dissolved in 5 mL of a 75% aqueous ethanol solution, and about 0.5 mg of rosuvastatin was added thereto and then completely dissolved. About 0.5 mg of rosuvastatin alone was completely dissolved in 5 mL of a 75% aqueous ethanol solution as a control group for the compatibility evaluation. Each of the resulting solutions was vacuum-dried at about 50° C. for about 24 hours to completely remove the solvent, thereby preparing a test sample. While each test temple was stored under severe conditions (at a temperature of about 60° C. and a relative humidity of about 85%), a degree of generation of related compounds with time was observed. The related compounds were analyzed by high-performance liquid chromatography (HPLC) in the following manner.

<Rosuvastatin Analysis Method>

The test sample was dissolved in 25 mL of methanol, followed by a 2-fold dilution with a mobile phase and filtration through a 0.45-um filter, thereby preparing an analysis sample.

<HPLC Conditions>

Column; C18, 250×4.6 mm, 5 um

Mobile phase; Acetonitrile: 0.5% (v/v) aqueous formic acid solution=50:50

Flow rate: 1 mL/min

Injection volume: 20 uL

Temperature: 40° C.

Wavelength: 248 nm

The amounts of related compounds generated on the $1^{st}$ week and $3^{rd}$ week are shown in Table 1.

TABLE 1

| Example | Coating material | Related compound (%, $1^{st}$ week) | Related compound (%, $3^{rd}$ week) |
| --- | --- | --- | --- |
| 1-1 | Polyethylene glycol 10000 | 1.5 | 5.9 |
| 1-2 | Poloxamer 188 | 5.6 | 14.8 |
| 1-3 | Poloxamer 407 | 12 | 24.3 |
| 1-4 | Cremophor | 1.0 | 8.9 |
| 1-5 | Polyvinyl pyrrolidone | 2.7 | 16.0 |
| 1-6 | Cremophor A25 | 2.5 | 9.0 |
| 1-7 | Ethyl cellulose CP10 | 0.2 | 1.0 |
| 1-8 | Ethyl cellulose CP45 | 0 | 0.01 |
| 1-9 | Sodium alginate | 0.6 | 16.0 |
| 1-10 | Eudragit L100 | 78.7 | 92.1 |
| 1-11 | Hydroxypropyl methyl cellulose (HPMC) | 0 | 0 |
| 1-12 | Polysorbate | 22 | 23.2 |
| 1-13 | Solutol HS15 | 20 | 22.4 |
| 1-14 | Gelucire 14/44 | 9.1 | 31.5 |
| 1-15 | Polyvinyl alcohol | 0.5 | 0.7 |
| Control group | Rosuvastatin | 1.4 | 5.2 |

Referring to Table 1, when rosuvastatin was stored under the severe conditions, the amounts of generated related compounds were gradually increased with time. About 1.4% of related compounds and about 5.4% of related compounds were generated after the storage for 1 week and 3 weeks, respectively. However, when each of hydroxypropyl methyl cellulose (HPMC), ethyl cellulose, and polyvinyl alcohol was used, generation of related compounds were significantly inhibited, indicating good compatibility of rosuvastatin with HPMC, ethyl cellulose, and polyvinyl alcohol.

EXAMPLE 2

Evaluation of Compatibility of Atorvastatin and Coating Material

To form an atorvastatin-containing drug-coating layer, compatibility of atorvastatin with various coating materials (coating agents and surfactants) were evaluated. About 2.5 mg of each coating material as shown in Table 2 was dissolved in 5 mL of a 75% aqueous ethanol solution, and about 0.5 mg of atorvastatin was added thereto and then completely dissolved. About 0.5 mg of atorvastatin was completely dissolved in 5 mL of a 75% aqueous ethanol solution as a control group for the compatibility evaluation. Each of the resulting solutions was vacuum-dried at about 50° C. for about 24 hours to completely remove the solvent, thereby preparing test samples. While each test temple was stored under severe conditions (at a temperature of about 60° C. and a relative humidity of about 85%), a degree of generation of related compounds with time was observed. The related compounds were analyzed by HPLC in the following manner.

<Atorvastatin Analysis Method>

Each test sample was dissolved in 25 mL of methanol, followed by a 2-fold dilution with a mobile phase and filtration through a 0.45-um filter, thereby preparing analysis samples.

<HPLC Conditions>

Column; C18, 250×4.6 mm, 5 um

Mobile phase; acetonitrile: 0.5% (v/v) aqueous formic acid solution=50:50

Flow rate; 1 mL/min

Injection volume; 20 uL

Temperature; 40° C.

Wavelength; 248 nm

The results of analyzing the amounts of related compounds generated on the $1^{st}$ week and $3^{rd}$ week are shown in Table 2.

TABLE 2

| Example | Coating material | Related compound (%, $1^{st}$ week) | Related compound (%, $3^{rd}$ week) |
| --- | --- | --- | --- |
| 2-1 | Polyethylene glycol 10000 | 0 | 0 |
| 2-2 | Poloxamer 188 | 23.3 | 29.4 |
| 2-3 | Poloxamer 407 | 12.7 | 16.3 |
| 2-4 | Cremophor | 1.4 | 2.2 |
| 2-5 | Polyvinyl pyrrolidone | 3.0 | 3.4 |
| 2-6 | Cremophor A25 | 14.3 | 17.7 |
| 2-7 | Ethyl cellulose CP10 | 1.7 | 0.9 |
| 2-8 | Ethyl cellulose CP45 | 1.2 | 1.3 |
| 2-9 | Sodium alginate | 0.5 | 0 |
| 2-10 | Eudragit L100 | 98 | 98 |
| 2-11 | Hydroxypropyl methyl cellulose (HPMC) | 0 | 0 |
| 2-12 | Polysorbate | 30 | 28.5 |
| 2-13 | Solutol HS15 | 8.4 | 9.2 |
| 2-14 | Gelucire 14/44 | — | 94.6 |
| 2-15 | Polyvinyl alcohol | 0.1 | 0.3 |
| Control group | Atorvastatin | 0.3 | 3.3 |

Referring to Table 2, when atorvastatin was stored under the severe conditions, the amounts of generated related compounds were gradually increased with time. About 0.3% of related compounds and about 3.3% of related compounds were generated after the storage for 1 week and 3 weeks, respectively. However, when each of polyethylene glycol, sodium alginate, HPMC, and polyvinyl alcohol was used, generation of related compounds were significantly inhibited, indicating good compatibility of atorvastatin with polyethylene glycol, sodium alginate, HPMC, and polyvinyl alcohol.

EXAMPLE 3

Evaluation of Compatibility of Pitavastatin and Coating Material

To form a pitavastatin-containing drug-coating layer, compatibility of pitavastatin with various coating materials (coating agents and surfactants) were evaluated. About 2.5 mg of each coating material as shown in Table 3 was dissolved in 5 mL of a 75% aqueous ethanol solution, and about 0.5 mg of pitavastatin was added thereto and then completely dissolved. About 0.5 mg of pitavastatin alone was completely dissolved in 5 mL of a 75% aqueous ethanol solution as a control group for the compatibility evaluation. Each of the resulting solutions was vacuum-dried at about 50° C. for about 24 hours to completely remove the solvent, thereby preparing test samples. While each test temple was stored under severe conditions (at a temperature of about 60° C. and a relative humidity of about 85%), a degree of generated related compounds with time was observed. The related compounds were analyzed by HPLC in the following manner.

<Pitavastatin Analysis Method>

Each test sample was dissolved in 25 mL of methanol, followed by a 2-fold dilution with a mobile phase and filtration through a 0.45-um filter, thereby preparing analysis samples.

<HPLC Conditions>

Column; C18, 250×4.6 mm, 5 um

Mobile phase; acetonitrile: 0.1% (v/v) aqueous trifluoroacetic acid (TFA) solution=60:40

Flow rate; 1 mL/min

Injection volume; 20 uL

Temperature; 40° C.

Wavelength; 245 nm

The results of analyzing the amounts of related compounds generated on the $1^{st}$ week and $3^{rd}$ week are shown in Table 3.

TABLE 3

| Example | Coating material | Related compound (%, $1^{st}$ week) | Related compound (%, $3^{rd}$ week) |
|---|---|---|---|
| 3-1 | Polyethylene glycol 10000 | 8.3 | 13.9 |
| 3-2 | Poloxamer 188 | 3.6 | 6.0 |
| 3-3 | Poloxamer 407 | 12.2 | 25.7 |
| 3-4 | Cremophor A25 | 7.2 | 21.7 |
| 3-5 | Ethyl cellulose CP45 | 0.2 | 0.4 |
| 3-6 | Sodium alginate | 0 | 0.5 |
| 3-7 | Eudragit L100 | 88 | 85 |
| 3-8 | Hydroxypropyl methyl cellulose (HPMC) | 0.5 | 0.1 |
| 3-9 | Polyvinyl pyrrolidone | 2.5 | 28.5 |
| 3-10 | Polyvinyl alcohol | 0.2 | 0.5 |
| Control group | Pitavastatin | 0.1 | 0.2 |

Referring to Table 3, when pitavastatin was stored under the severe conditions, the amounts of generated related compounds were gradually increased with time. About 0.1% of related compounds and about 0.2% of related compounds were generated after the storage for 1 week and 3 weeks, respectively. However, when HPMC was used, generation of related compounds was significantly inhibited, indicating good compatibility of pitavastatin with HPMC.

EXAMPLE 4

Evaluation of Shield Coating Layer

Coating solutions including a statin-based drug were prepared based on the results of Examples 1 to 3, and each then coated on a gelatin capsule core including an omega-3-fatty acid by aqueous coating. However, gelatin capsule cores were adhered to one another during the aqueous coating, and shapes of the gelatin capsule cores were so deformed at a coating temperature that a drug-coating layer, including a statin-based drug was not successfully formed. Accordingly, shield coating layers were formed using various coating materials on the gelatin capsule core, and quality thereof were evaluated. Capsules in multilayer-coated form, each including a shield coating layer formed using coating agents having relatively better physical characteristics, for example, hydroxypropyl methyl cellulose (HPMC), ethyl cellulose, Eudragit E 100, Eudragit E PO, or a combination thereof, were prepared, and physical characteristics (disintegrability and stability) thereof were evaluated.

1. Preparation of Capsule in Multilayer-Coated Form (1) Formation of Gelatin Capsule Core Including Omega-3-Acid Ethyl Ester A gelatin film consisting of gelatin, water, and glycerin was filled with about 1,000 g of an omega-3-acid ethyl ester per one batch, and dried at about 40° C. for about 72 hours to remove the remaining water from the gelatin thin film, thereby forming a gelatin capsule core. Each of the obtained gelatin capsule core (i.e. per one capsule) included about 1,000 mg of omega-3-acid ethyl ester, about 293 mg of gelatin, and about 135 mg of glycerin. A total weight of each capsule was 1,428 mg (per one capsule).

First, second, and third coating layers each having the composition as shown in Table 4 were formed on each gelatin capsule core as stated below. In Table 4, the amounts of ingredients are in milligrams (mg) per unit capsule.

(2) Formation of First Coating Layer (Shield Coating Layer)

Coating solutions for the first coating layer were prepared by dissolving coating materials as shown in Table 4 in 300 mL of a 75% aqueous ethanol solution. Gelatin capsule cores prepared in Section (1) above were put into a pan coating machine, and then coated with each coating solution by spraying. The coating conditions were as follows:

<Coating Conditions>

Coating pan speed; 10±2 rpm

Inlet air pan speed; 1200±200 rpm

Outlet air pan speed; 2000±200 rpm

Inlet air temperature; 30±3° C.

Outlet air temperature; 28±3° C.

Coating solution spray rate; 20±5 mL/min

After completion of spraying the coating solution, further drying was performed in the pan coating machine for about 1 hour to remove the remaining solvent (3) Formation of Second Coating Layer and Third Coating Layer Coating solutions for the second coating layer were prepared by dissolving atorvastatin and HPMC as shown in Table 4 in 500 mL of a 20% aqueous ethanol solution. Capsules with a first coating layer as formed in Section (2) above were put into a pan coating machine, and then coated with its corresponding coating solution for the second coating layer by spraying. The coating conditions were as follows:

<Coating Conditions>

Coating pan speed; 10±2 rpm

Inlet air pan speed; 1200±200 rpm

Outlet air pan speed; 2000±200 rpm

Inlet air temperature; 30±3° C.

Outlet air temperature; 28±3° C.

Coating solution spray rate; 10±5 mL/min

Coating solutions for the third coating layer were prepared by dissolving HPMC (HPMC and Eudragit E PO in Example 4-7) as shown in Table 4 in 500 mL of a 50% aqueous ethanol solution. Capsules with a second coating layer as formed in Section (2) above were put into a pan coating machine, and then coated with its corresponding coating solution for the third coating layer by spraying. The coating conditions were as follows:

<Coating Conditions>
Coating pan speed; 10±2 rpm
Inlet air pan speed; 1200±200 rpm
Outlet air pan speed; 2000±200 rpm
Inlet air temperature; 28±3° C.
Outlet air temperature; 30±3° C.
Coating solution spray rate; 20±5 mL/min

TABLE 4

|  | Coating material | Comparative Example | | Example | | | | | | |
|---|---|---|---|---|---|---|---|---|---|---|
|  |  | 4-1 | 4-2 | 4-1 | 4-2 | 4-3 | 4-4 | 4-5 | 4-6 | 4-7 |
| First coating layer | Hydroxypropyl methyl cellulose | 30 | — | 15 | 10 | 6 | 3 | 6 | 6 | 15 |
|  | Ethyl cellulose | — | 30 | — | — | — | — | — | — | — |
|  | Eudragit E PO | — | — | 15 | 20 | 24 | 27 | — | 24 | 15 |
|  | Eudragit E 100 | — | — | — | — | — | — | 24 | — | — |
| Second coating layer | Atorvastatin | 5 | 5 | 5 | 5 | 5 | 5 | 5 | 5 | 5 |
|  | Hydroxypropyl methyl cellulose | 25 | 25 | 25 | 25 | 25 | 25 | 25 | 50 | 25 |
| Third coating layer | Hydroxypropyl methyl cellulose | 20 | 20 | 20 | 20 | 20 | 20 | 20 | 12.5 | 10 |
|  | Eudragit E PO | — | — | — | — | — | — | — | — | 10 |

2. Evaluation on Disintegration and Stability of Capsule in Multilayer-Coated Form (1) Disintegration Test A disintegration time of each of the capsules in multilayer-coated form was measured in a pH 1.2 aqueous solution at about 37° C. in accordance with the disintegration test method in the general test of the Korean Pharmacopoeia. For comparison, a disintegration time of a commercially available omega-3-acid ethyl ester 90 capsules (Omacor™) was measured under the same conditions. The results are shown in Table 5.

TABLE 5

| Example | Disintegration time |
|---|---|
| Omacor ™ | 6-7 min |
| Comparative Example 4-1 | 7-8 min |
| Comparative Example 4-2 | 30 min or more |
| Example 4-1 | 7-8 min |
| Example 4-2 | 7-8 min |
| Example 4-3 | 7-9 min |
| Example 4-4 | 7-8 min |
| Example 4-5 | 8 min |
| Example 4-6 | 8 min |
| Example 4-7 | 7-8 min |

Referring to Table 5, the capsules in multilayer-coated form of Examples 4-1 to 4-7 and Comparative Example 4-1 were all found to have similar disintegration time as the reference formulation (Omacor™). However, the capsules in which ethyl cellulose was included in the first coating layer, had significantly longer disintegration time than the other formulations, indicating that ethyl cellulose may have a significant influence on the absorption pattern in the gastrointestinal tract when the capsules made therefrom orally administrated.

(2) Stability Test

After storing the capsules in multilayer-coated form prepared above under acceleration conditions (at a temperature of about 40° C. and a relative humidity of about 75%) for 6 months, the generation and amount changes of related compounds were analyzed by HPLC. The results are shown in Table 6.

TABLE 6

| Storage time | Comparative Example | | Example | | | | | | |
|---|---|---|---|---|---|---|---|---|---|
|  | 4-1 | 4-2 | 4-1 | 4-2 | 4-3 | 4-4 | 4-5 | 4-6 | 4-7 |
| Initial | 0.2 | 0.2 | 0.2 | 0.2 | 0.2 | 0.2 | 0.2 | 0.2 | 0.2 |
| 1 month | 0.7 | 0.3 | 0.3 | 0.2 | 0.2 | 0.2 | 0.2 | 0.2 | 0.2 |

TABLE 6-continued

| Storage time | Comparative Example | | Example | | | | | | |
|---|---|---|---|---|---|---|---|---|---|
|  | 4-1 | 4-2 | 4-1 | 4-2 | 4-3 | 4-4 | 4-5 | 4-6 | 4-7 |
| 3 months | 2.1 | 0.4 | 0.3 | 0.3 | 0.2 | 0.3 | 0.3 | 0.3 | 0.3 |
| 6 months | 5.3 | 0.7 | 0.6 | 0.5 | 0.4 | 0.4 | 0.4 | 0.4 | 0.4 |

Referring to Table 6, in the capsules in which only HPMC was used in the first coating layer, large amounts of related compounds were generated.

The results of Tables 5 and 6 indicates that forming a shield coating layer from a mixture of HPMC, and Eudragit E 100 or Eudragit E PO, i.e., a mixture of HPMC and a copolymer of butyl methacrylate, (2-demethylaminoethyl) methacrylate, and methyl methacrylate at a weight ratio of 1:2:1 may be appropriate in terms of disintegration and stability of the capsules.

EXAMPLE 5

Preparation of a Pharmaceutical Composition in Multilayer-Coated Form Including Omega-3-Acid Ethyl Ester and Atorvastatin Pharmaceutical compositions in multilayer-coated form including omega-3-acid ethyl ester and atorvastatin were prepared according to the compositions of first, second, and third coating layers as shown in Table 7. In Table 7, the amounts of ingredients are in milligrams (mg) per one capsule prepared. The preparation method of the pharmaceutical compositions for oral administration in multilayer-coated form was the same as in Section 1 of Example 4, except that the coating solution for the second coating layer was prepared by additionally dissolving a stabilizer (such as sodium bicarbonate, magnesium oxide, calcium silicate, sodium citrate, or sodium phosphate, or the like), an adsorbant (sodium oleate, or the like), or a pH adjuster (sodium hydroxide, or the like) and that the coating solution for the third coating layer was prepared by additionally dissolving a pigment (Red 40).

TABLE 7

|  | Coating material | Example 5-1 | 5-2 | 5-3 | 5-4 | 5-5 | 5-6 | 5-7 |
|---|---|---|---|---|---|---|---|---|
| First coating layer | HPMC | 6 | 6 | 6 | 6 | 6 | 6 | 6 |
|  | Eudragit E PO | 24 | 24 | 24 | 24 | 24 | 24 | 24 |
| Second coating layer | Atorvastatin | 5 | 5 | 5 | 5 | 5 | 5 | 5 |
|  | HPMC | 50 | 50 | 50 | 50 | 50 | 50 | 50 |
|  | Sodium bicarbonate | 5 | — | — | — | — | — | — |
|  | Magnesium oxide | — | 2.5 | — | — | — | — | — |
|  | Sodium citrate | — | — | 5 | — | — | — | — |
|  | Sodium phosphate | — | — | — | 5 | — | — | — |
|  | Calcium silicate | — | — | — | — | 1 | — | — |
|  | Sodium oleate | — | — | — | — | — | 5 | — |
|  | Sodium hydroxide | — | — | — | — | — | — | 2.5 |
| Third coating layer | HPMC | 24 | 24 | 24 | 24 | 24 | 24 | 24 |
|  | Eudragit E PO | 6 | 6 | 6 | 6 | 6 | 6 | 6 |
|  | Red 40 | Suitable amount | Suitable amount | Suitable amount | Suitable amount | Suitable amount | Suitable amount | Suitable amount |

EXAMPLE 6

Preparation of Pharmaceutical Composition in Multilayer-Coated Form Including Omega-3-Acid Ethyl Ester and Rosuvastatin Pharmaceutical compositions in multilayer-coated form including omega-3-acid ethyl ester and rosuvastatin were prepared according to the compositions of first, second, and third coating layers as shown in Table 8. In Table 8, the amounts of ingredients are in milligrams (mg) per one capsule prepared.

A gelatin capsule core including about 1,000 mg of omega-3-acid ethyl ester, and a shield coating layer (first coating layer) on the gelatin capsule core were formed in the same manner as in Sections 1(1) and 1(2) of Example 4, respectively. The coating solutions for the second coating layer were prepared by dissolving rosuvastatin and a coating material (HPMC, ethyl cellulose, or polyvinyl alcohol) in 500 mL of a 20% aqueous ethanol solution. The coating solutions for the second coating layer of Examples 6-4 to 6-6 were prepared by additionally dissolving di-alpha-tocopheryl polyethylene glycol 1000 succinate (TPGS) as an antioxidant. The coating solutions for the second coating layer of Examples 6-7 and 6-8 were prepared by additionally dissolving a stabilizer (sodium citrate or the like) and a pH adjuster (sodium hydroxide or the like), respectively. Capsules with a first coating layer were put into a pan coating machine, and then coated with its corresponding coating solution for the second coating layer by spraying. The coating conditions were as follows:

<Coating Conditions>
Coating pan speed 10±2 rpm
Inlet air pan speed; 1200±200 rpm
Outlet air pan speed; 2000±200 rpm
Inlet air temperature; 30±3° C.
Outlet air temperature; 28±3° C.
Coating solution spray rate; 10±5 mL/min Coating solutions for the third coating layer were prepared by dissolving HPMC, Eudragit E PO, or polyvinyl acetate (PVAc), together with a light-shielding agent, in 500 mL of a 50% aqueous ethanol solution. Capsules with a second coating layer were put into a pan coating machine, and then coated with its corresponding coating solution for the third coating layer by spraying. The coating conditions were as follows:

<Coating Conditions>
Coating pan speed; 10±2 rpm
Inlet air pan speed; 1200±200 rpm
Outlet air pan speed; 2000±200 rpm
Inlet air temperature; 28±3° C.
Outlet air temperature; 30±3° C.
Coating solution spray rate; 20±5 mL/min

TABLE 8

|  | Coating material | Example 6-1 | 6-2 | 6-3 | 6-4 | 6-5 | 6-6 | 6-7 | 6-8 |
|---|---|---|---|---|---|---|---|---|---|
| First coating layer | HPMC | 6 | 6 | 6 | 6 | 6 | 6 | 6 | 6 |
|  | Eudragit E PO | 24 | 24 | 24 | 24 | 24 | 24 | 24 | 24 |
| Second coating layer | Rosuvastatin | 5 | 5 | 5 | 5 | 5 | 5 | 5 | 5 |
|  | HPMC | 50 | — | — | 50 | — | 50 | 50 | 50 |
|  | Ethyl cellulose | — | 50 | — | — | 50 | — | — | — |
|  | Polyvinyl alcohol | — | — | 50 | — | — | — | — | — |
|  | TPGS | — | — | — | 5 | 5 | 5 | — | — |
|  | Sodium citrate | — | — | — | — | — | — | 5 | — |
|  | Sodium hydroxide | — | — | — | — | — | — | — | 2.5 |
| Third coating layer | Titanium oxide | 20 | 20 | 20 | 20 | 20 | 20 | — | — |
|  | HPMC | 50 | 50 | 50 | 50 | 50 | — | 24 | 24 |
|  | PVAc | — | — | — | — | — | 50 | — | — |
|  | Eudragit E PO | — | — | — | — | — | — | 6 | 6 |

EXAMPLE 7

Preparation of Pharmaceutical Composition in Multilayer-Coated Form Including Omega-3-Acid Ethyl Ester and Pitavastatin Pharmaceutical compositions in multilayer-coated form including omega-3-acid ethyl ester and pitavastatin were prepared according to the compositions of first, second, and third coating layers as shown in Table 9. In Table 9, the amounts of ingredients are in milligrams (mg) per one capsule prepared.

A gelatin capsule core including about 1,000 mg of omega-3-acid ethyl ester, and a shield coating layer (first coating layer) on the gelatin capsule core were formed in the same manner as in Sections 1(1) and 1(2) of Example 4, respectively. The coating solutions for the second coating layer were prepared by dissolving pitavastatin and HPMC in 500 mL of a 20% aqueous ethanol solution. The coating solutions for the second coating layer of Examples 7-2 and 7-3 were prepared by additionally dissolving di-alpha-tocopheryl polyethylene glycol 1000 succinate (TPGS) as an antioxidant. The coating solutions for the second coating layer of Examples 7-4 to 7-6 were prepared by additionally dissolving a stabilizer (sodium bicarbonate or the like) or an adsorbant (sodium oleate or the like). Capsules with a first coating layer were put into a pan coating machine, and then coated with its corresponding coating solution for the second coating layer by spraying. The coating conditions were as follows:

<Coating Conditions>
Coating pan speed; 10±2 rpm
Inlet air pan speed; 1200±200 rpm
Outlet air pan speed; 2000±200 rpm
Inlet air temperature; 30±3° C.
Outlet air temperature; 28±3° C.
Coating solution spray rate; 10±5 mL/min Coating solutions for the third coating layer were prepared by dissolving HPMC, Eudragit E PO, or polyvinyl acetate (PVAc), together with a light-shielding agent, in 500 mL of a 50% aqueous ethanol solution. Capsules with a second coating layer were put into a pan coating machine, and then coated with its corresponding coating solution for the third coating layer by spraying. The coating conditions were as follows:

<Coating Conditions>
Coating pan speed; 10±2 rpm
Inlet air pan speed; 1200±200 rpm
Outlet air pan speed; 2000±200 rpm
Inlet air temperature; 28±3° C.
Outlet air temperature; 30±3° C.
Coating solution spray rate; 20±5 mL/min

TABLE 9

| | Coating material | 7-1 | 7-2 | 7-3 | 7-4 | 7-5 | 7-6 |
|---|---|---|---|---|---|---|---|
| First coating layer | HPMC | 6 | 6 | 6 | 6 | 6 | 6 |
| | Eudragit E PO | 24 | 24 | 24 | 24 | 24 | 24 |
| Second coating layer | Pitavastatin | 2 | 2 | 2 | 2 | 2 | 2 |
| | HPMC | 20 | 20 | 20 | 20 | 20 | 20 |
| | TPGS | — | 5 | 5 | — | — | — |
| | Sodium bicarbonate | — | — | — | 2.5 | — | — |
| | Magnesium oxide | — | — | — | — | 1 | — |
| | Sodium oleate | — | — | — | — | — | 2.5 |
| Third coating layer | Titanium oxide | 20 | 20 | 20 | — | — | — |
| | HPMC | 50 | 50 | — | 24 | 24 | 24 |
| | PVAc | — | — | 50 | — | — | — |
| | Eudragit E PO | — | — | — | 6 | 6 | 6 |

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present disclosure have been described with reference to the figures, it will be understood by those of ordinary skill in the art that various changes in form and details may be made therein without departing from the spirit and scope of the present disclosure as defined by the following claims.

What is claimed is:

1. A pharmaceutical composition for oral administration, comprising:
    (a) a gelatin capsule core containing an omega-3 fatty acid or an alkyl ester thereof;
    (b) a first coating layer formed by coating, on the gelatin capsule core, hydroxypropyl methyl cellulose and a copolymer of butyl methacrylate, (2-demethylaminoethyl) methacrylate, and methyl methacrylate at a weight ratio of 1:2:1; wherein a weight ratio of the hydroxypropyl methyl cellulose and the copolymer of butyl methacrylate, (2-demethylaminoethyl) methacrylate, and methyl methacrylate at a weight ratio of 1:2:1 in the first coating layer is in a range of about 1:0.8 to about 1:10; and
    (c) a second coating layer formed by coating, on the first coating layer, a coating solution containing a statin-based drug.

2. The pharmaceutical composition for oral administration of claim 1, wherein the alkyl ester of an omega-3 fatty acid is an ethyl ester of an omega-3 fatty acid.

3. The pharmaceutical composition for oral administration of claim 1, wherein a weight ratio of the hydroxypropyl methyl cellulose and the copolymer of butyl methacrylate, (2-demethylaminoethyl) methacrylate, and methyl methacrylate at a weight ratio of 1:2:1 in the first coating layer is in a range of about 1:1 to about 1:9.

4. The pharmaceutical composition for oral administration of claim 1, wherein the coating solution containing a statin-based drug is obtained by dissolving atorvastatin or a salt thereof, and at least one coating agent selected from the group consisting of polyethylene glycol, sodium alginate, hydroxypropyl methyl cellulose, and polyvinyl alcohol in water, ethanol, or an aqueous ethanol solution.

5. The pharmaceutical composition for oral administration of claim 4, wherein the amount of the coating agent is in a range of about 1 part by weight to about 20 parts by weight based on 1 part by weight of the atorvastatin or a salt thereof.

6. The pharmaceutical composition for oral administration of claim 1, wherein the coating solution containing a statin-based drug is obtained by dissolving rosuvastatin or a salt thereof, and at least one coating agent selected from the group consisting of hydroxypropyl methyl cellulose, ethyl cellulose, and polyvinyl alcohol in water, ethanol, or an aqueous ethanol solution.

7. The pharmaceutical composition for oral administration of claim 6, wherein the amount of the coating agent is in a range of about 1 part to about 20 parts by weight based on 1 part by weight of the rosuvastatin or a salt thereof.

8. The pharmaceutical composition for oral administration of claim 1, wherein the coating solution containing a statin-based drug is obtained by dissolving pitavastatin or a salt thereof and hydroxypropyl methyl cellulose in water, ethanol, or an aqueous ethanol solution.

9. The pharmaceutical composition for oral administration of claim 8, wherein the amount of the hydroxypropyl methyl cellulose is in a range of about 1 part to about 50 parts by weight based on 1 part by weight of the pitavastatin or a salt thereof.

10. The pharmaceutical composition for oral administration of claim 1, wherein the second coating layer further comprises at least one antioxidant selected from the group consisting of tocopherol, di-alpha-tocopheryl polyethylene glycol 1000 succinate, and tocopheryl acetate.

11. The pharmaceutical composition for oral administration of claim 10, wherein the amount of the antioxidant is in a range of about 0.1 part to about 1 part by weight based on 1 part by weight of the statin-based drug.

12. The pharmaceutical composition for oral administration according to claim 1 further comprising a third coating layer formed by coating, on the second coating layer, a coating solution containing at least one coating agent selected from the group consisting of hydroxypropyl cellulose, hydroxypropyl methyl cellulose, a copolymer of butyl methacrylate, (2-demethylaminoethyl) methacrylate, and methyl methacrylate at a weight ratio of 1:2:1, carboxymethyl cellulose, polyvinyl alcohol-polyethylene glycol copolymer, polyvinyl acetate, and polyvinyl alcohol.

13. The pharmaceutical composition for oral administration of claim 12, wherein the coating solution for the third coating layer further comprises at least one light-shielding agent selected from the group consisting of talc, carnauba wax, ethyl vanillin, titanium oxide, and iron oxide.

14. The pharmaceutical composition for oral administration according to claim 11 further comprising a third coating layer formed by coating, on the second coating layer, a coating solution containing at least one coating agent selected from the group consisting of hydroxypropyl cellulose, hydroxypropyl methyl cellulose, a copolymer of butyl methacrylate, (2-demethylaminoeethyl) methacrylate, and methyl methacrylate at a weight ratio of 1:2:1, carboxymethyl cellulose, polyvinyl alcohol-polyethylene glycol copolymer, polyvinyl acetate, and polyvinyl alcohol.

\* \* \* \* \*